United States Patent [19]
Pirl

[11] Patent Number: 5,174,165
[45] Date of Patent: Dec. 29, 1992

[54] FLEXIBLE DELIVERY SYSTEM FOR A ROTATABLE PROBE

[75] Inventor: William E. Pirl, Levelgreen, Pa.

[73] Assignee: Westinghouse Electric Corp., Pittsburgh, Pa.

[21] Appl. No.: 873,516

[22] Filed: Apr. 21, 1992

Related U.S. Application Data

[63] Continuation of Ser. No. 566,001, Aug. 13, 1990, abandoned.

[51] Int. Cl.⁵ .................. G01M 19/00; G21C 17/017
[52] U.S. Cl. .................................. 73/866.5; 324/220; 376/249
[58] Field of Search ................. 73/865.5, 865.8, 865.9; 324/220, 221; 376/249

[56] References Cited

U.S. PATENT DOCUMENTS

| | | | |
|---|---|---|---|
| 4,050,384 | 9/1977 | Chapman | 73/40.5 R X |
| 4,052,686 | 10/1977 | Schmitz | 73/866.5 X |
| 4,481,814 | 11/1984 | Wentzell | 73/866.5 |
| 4,494,907 | 1/1985 | Coussau et al. | 414/749 |
| 4,505,323 | 3/1985 | de la Pintiere et al. | 165/11 A |
| 4,679,448 | 7/1987 | Lund | 73/866.5 |
| 4,690,006 | 9/1987 | Urata | 73/866.5 |
| 4,703,264 | 10/1987 | Edwards | 324/220 |
| 4,760,749 | 8/1988 | Grouleau | 73/866.5 |
| 4,806,863 | 2/1989 | White | 324/238 |
| 4,848,168 | 7/1989 | Negishi | 73/866.5 U X |
| 4,856,354 | 8/1989 | Overbay | 73/866.5 |
| 4,936,307 | 6/1990 | Saito et al. | 128/662.06 |
| 4,951,677 | 8/1990 | Crowley et al. | 128/662.06 |
| 4,981,044 | 1/1991 | Adams et al. | 73/623 |
| 5,105,876 | 4/1992 | Burack et al. | 73/865.8 X |

FOREIGN PATENT DOCUMENTS

| | | | |
|---|---|---|---|
| 3035502 | 4/1982 | Fed. Rep. of Germany | 73/866.5 |
| 2613835 | 10/1988 | France | |
| 75618 | 6/1980 | Japan | 73/866.5 |
| 288153 | 12/1986 | Japan | 73/866.5 |
| 191058 | 8/1988 | Japan | 73/866.5 |
| 210659 | 9/1988 | Japan | 73/866.5 |
| 1488833 | 10/1977 | United Kingdom | |

OTHER PUBLICATIONS

European Search Report EP 91 30 7463, The Hague, Bosma R.A.P. (Search report completed Oct. 16, 1991).

*Primary Examiner*—Tom Noland

[57] ABSTRACT

A flexible, hose-like delivery system for positioning and rotatably supporting a probe which may be a pancake-type eddy current probe at a desired position along the longitudinal axis of a small-diametered conduit such as the heat exchanger tube in a nuclear steam generator is disclosed. The system comprises a flexible inner shaft formed from a plurality of short segments of Bowden shafting which is connected to a drive train located remotely from the interior of the heat exchanger tube, a flexible outer housing preferably formed from a plastic conduit concentrically disposed around the inner shaft, and a plurality of ball bearing assemblies which interconnect the short shaft segments for minimizing the frictional engagement between the inner shaft and the interior walls of the flexible outer housing. The frictional losses between the inner shaft and the flexible tubular outer housing are small enough to allow rotational motion to be smoothly and reliably conducted over relatively long lengths and around bends, thus allowing such motion to be transmitted by remotely located, standard-sized drive trains and motors. The system eliminates the need for expensive, miniaturized drive trains, motors and slip ring components which, up to now, have accompanied such eddy current probes within such tubes.

25 Claims, 6 Drawing Sheets

FLEXIBLE DELIVERY SYSTEM FOR A ROTATABLE PROBE

This application is a continuation, of application Ser. No. 07/566,001 filed Aug. 13, 1990 and now abandoned.

BACKGROUND OF THE INVENTION

This invention generally relates to delivery systems for probes, and is specifically concerned with a flexible, hose-like delivery system for a pancake-type eddy current coil capable of remotely and reliably transmitting rotational motion through a small-diametered conduit, such as the heat exchanger tube of a nuclear steam generator.

Systems for delivering and rotating probes for the inspection of small-diametered conduits are known in the prior art. Such systems are particularly useful in delivering and rotating pancake-type eddy current coils within the heat exchanger tubes of nuclear steam generators in order to inspect these tubes for faults such as cracks or wall thinning. However, before either the utility or the limitations of such systems can be fully appreciated, some general background as to the structure, operation and maintenance of nuclear steam generators is necessary.

Nuclear steam generators are generally comprised of a bowl-shaped primary side, a tubesheet disposed over the top of the primary side, and a cylindrically shaped secondary side which in turn is disposed over the tubesheet. Hot, radioactive water from the reactor core circulates through the primary side of the steam generator, while non-radioactive water is introduced into the secondary side. The tubesheet hydraulically isolates but thermally connects the primary side to the secondary side by means of a number of U-shaped heat exchanger tubes whose bottom ends are mounted in the tubesheet. Hot, radioactive water from the primary side flows through the interior of these heat exchanger tubes while the exterior of these tubes comes into contact with the non-radioactive water in the secondary side in order to generate non-radioactive steam.

In the secondary side of such steam generators, the legs of the U-shaped heat exchanger tubes extend through bores present in a plurality of horizontally-oriented support plates that are vertically spaced from one another, while the ends of these tubes are mounted within bores located in the tubesheet. Small, annular spaces are present between these heat exchanger tubes and the bores in the support plates and the tubesheet which are known in the art as "crevice regions". Such crevice regions provide only a very limited flowpath for the feedwater that circulates throughout the secondary side of the steam generator, which causes "dry boiling" to occur wherein the feedwater boils so rapidly that these regions can actually dry-out during the operation of the generator. This chronic drying-out causes impurities in the water to precipitate and collect in these crevice regions. These precipitates ultimately creates sludge and other debris that promote the occurrence of corrosion in the crevice regions which, if not repaired, can ultimately cause the tube to crack and to allow radioactive water from the primary side to contaminate the non-radioactive water in the secondary side of the generator.

Eddy current probe systems were developed to monitor the extent to which the walls of such heat exchanger tubes were degraded as a result of corrosion. One of the latest generations of such probes are known as "pancake-type" eddy current probes. Such probes comprise a cylindrical body that is insertable within the interior of the tube to be inspected, and a small, relatively flat circular coil mounted on the side of the probe body. The coil is resiliently biased radially into wiping engagement with the inner wall of the heat exchanger tube. In operation, a miniaturized motor (operating through a gear train), and lead screw simultaneously rotate and linearly advance the probe body so that the small flat pancake coil that is resiliently mounted on the side of the probe body scans the interior wall of the heat exchanger tubes along a helical path.

While such prior art eddy current coil systems have proven themselves to be an effective tool in accurately and reliably inspecting the inner walls of heat exchanger tubes for cracks, pits, wall thinning and other degradations which are caused by corrosion, the applicant has observed a number of areas where such systems could stand improvement. For example, the miniaturized motors, drive trains and electric slip rings contained within the bodies of such probes to create the necessary helical movement of the pancake coil are expensive, and require a considerable amount of effort to assemble within the narrow confines of the probe body, whose diameter can only be about 0.50 inches in a probe system capable of inspecting heat exchanger tubes having a 0.625 inch outer diameter. These expenses are compounded by the fact that the probe bodies and all related delivery conduits are typically discarded after a single maintenance operation in a nuclear power plant due to radiation contamination. But even if they were not so discarded, the applicant has noticed that the electrical load placed upon the relatively delicate windings of the miniaturized motors used to create the required helical motion can prematurely jeopardize the reliable operation of these motors, and can ultimately cause them to burn out well before their expected lifetimes.

One possible solution to some of the problems associated with the prior art would be the development of more powerful and reliable miniature motors. However, further developments in such motors would be a relatively costly and time consuming endeavor, and still would not solve the cost problems associated with the fact that the probe bodies and all associated delivery conduits are typically discarded after a single maintenance operation. Another possible solution might be to remotely drive the probe body by means of a flexible power shaft that is mechanically coupled to a motor located well outside of the heat exchanger tube being inspected. However, known flexible power shafts are not compatible with either the pusher-puller mechanisms used to extend and withdraw the probe body into and out of the radioactive primary side of the generator, or with the robotic arms typically used to insert and withdraw this probe body from a selected heat exchanger tube within the primary side. Such puller-pusher mechanisms employ opposing, motor-driven rollers which are resiliently mounted to engage and drive a cable that is connected to the proximal end of the probe body in order to move the probe into and out of the primary side, while robotic positioners use reciprocating gripper mechanisms for extending and retracting first the probe body and then the cable attached thereto into and out of a heat exchanger tube. The resilient rollers and grippers used in these mechanisms would mechanically interfere with the transmission of torque if the probe body were directly connected to a flexible, rotating shaft. Of course, a flexible, plastic conduit might be placed over the rotating shaft in order to prevent such interference from occurring. However, experience has shown that the friction that develops between the flexible, rotating shaft and the inner walls of any such covering greatly interferes with the smooth transmission of torque over the distances required to remotely rotate a probe disposed within a heat exchanger tube in a nuclear steam generator. Moreover, such known flexible shafts are insufficiently flexible to be wrapped around the reels used in conjunction with known pusher-puller mechanisms.

Clearly, what is needed is a flexible delivery system for positioning and rotatably driving a probe at a desired position within a conduit such as a heat exchanger tube which obviates the need for expensive miniaturized motors, drive trains and slip rings. It would be desirable if such a system were relatively inexpensive so that it could be discarded after becoming radioactively contaminated incident to a single inspection and maintenance operation without major cost. Finally, it would be desirable if such a system were compatible with known pusher-puller mechanisms and robotic positioning devices, and were simple in construction, and reliable and accurate in operation.

SUMMARY OF THE INVENTION

Generally speaking, the invention is a flexible delivery system for positioning and rotatably supporting a probe, such as a pancake-type eddy current probe, at a desired position along the longitudinal axis of a conduit that transcends the limitations associated with the prior art. This system is particularly well adapted for the delivery of a rotatable probe within a small-diametered conduit such as the heat exchanger tubes used in nuclear steam generators, and comprises a flexible inner shaft having a distal end connected to the probe and a proximal end remotely connected to a shaft rotating means such as an electric motor, a flexible outer housing concentrically disposed around the inner shaft, and a plurality of bearing assemblies disposed between the inner shaft and the outer housing for reducing friction when the inner shaft rotates with respect to the outer housing.

The flexible inner shaft is formed from a plurality of relatively short, flexible shaft segments, and the bearing assemblies include opposing coupling means, which may be threaded ends, for coupling together the shaft segments. An electrical cable is disposed within the flexible inner shaft for providing electrical current to the coil of the probe. The electrical cable rotates along with the inner shaft, and is connected to a source of electrical current (such as an eddy current generated) through a slip-ring connector located outside of the steam generator at the proximal end of the cable. In the preferred embodiment, each of the bearing assemblies includes a centrally disposed bore for conducting the cable, which may include a pair of coaxial cables, while each of the shaft segments is formed from a spring-like section of Bowden shafting whose hollow interior forms a natural passageway for such cables. Additionally, each of the bearing assemblies includes at least three and preferably five ball bearings for minimizing friction between the inner shaft, and the interior walls of the flexible outer housing.

One side of each ball bearing is rollingly received within a semi-spherical recess in its respective bearing assembly, while the other side directly and rollingly engages the inner wall of the flexible outer housing. Thus the ball bearings are able to rollingly engage the interior walls of the outer housing in the circumferential direction when the flexible inner shaft is rotated, and in the longitudinal direction when the flexible outer housing is bent. The short, highly flexible segments of Bowden shafting material, in combination with the peripherally disposed ball bearing present in each of the bearing assemblies, provides a hose-like delivery system which is flexible enough to be wound about a reel of the type used in connection with state-of-the-art pusher-puller assemblies, and which is further capable of remotely transmitting rotational motion from, for example, the shaft of a motor located outside of the steam generator with minimal frictional losses and with a maximum amount of smoothness at low rpms.

An encoder assembly is located at the distal end of the outer housing just beneath the probe so that the system operator may accurately monitor the rate at which the inner shaft rotates the probe. A thrust bearing is provided between the probe and the distal end of the outer housing to further minimize friction. At the proximal end of the outer housing, a drive train is connected to the proximal end of the flexible inner shaft for turning it at a desired rate of rotation.

The flexibility of the hose-like delivery system, in combination with the low frictional losses associated with the inner shaft that drives the probe, provides a delivery system wherein the drive train, motor, and slip ring assembly may be remotely located well outside of the conduit that the probe is inserted into, thereby obviating the need for expensive and relatively unreliable miniaturized components.

DETAILED DESCRIPTION OF THE PREFERRED EMBODIMENT

Figure 1A:
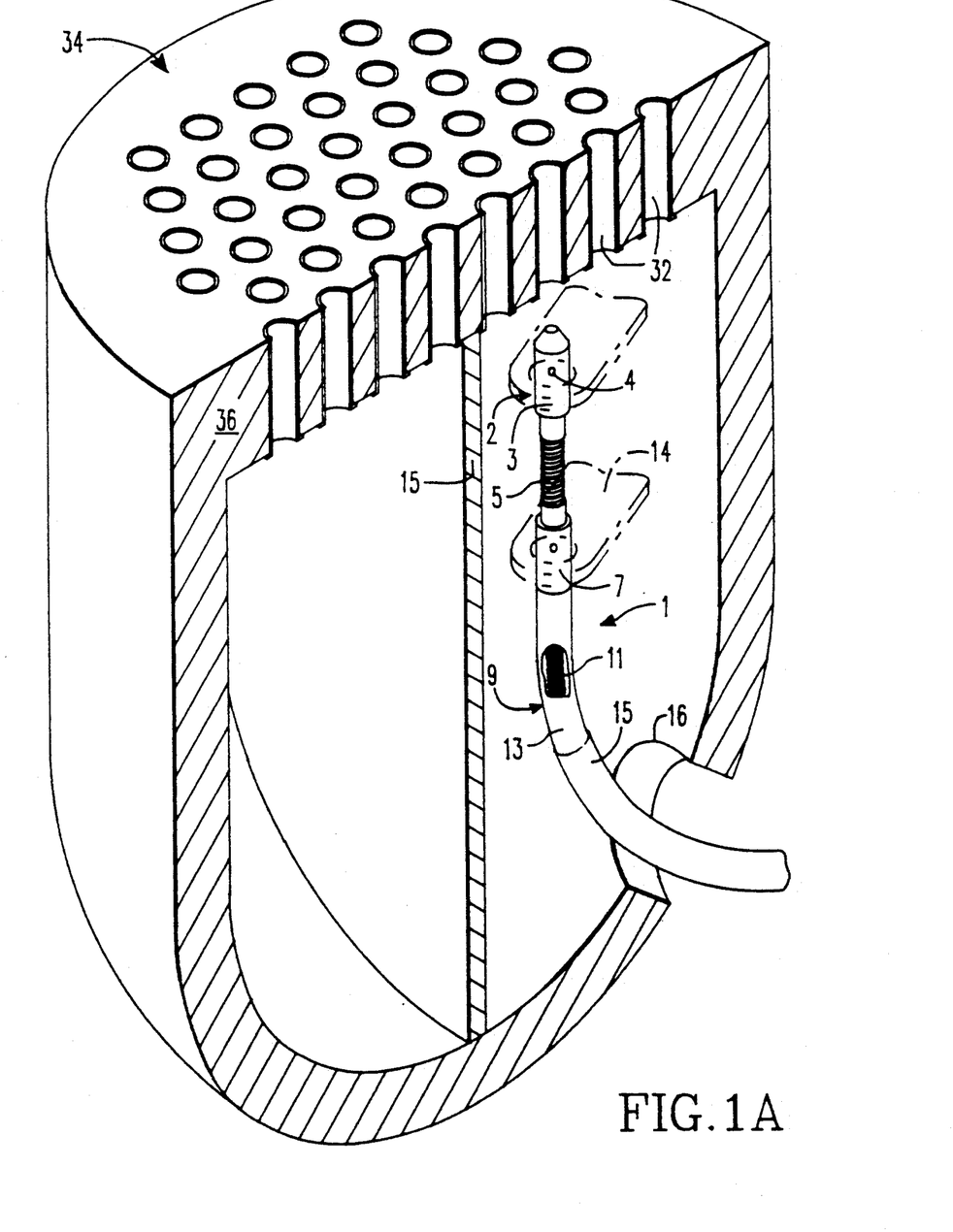
FIG. 1A is a perspective view of the proximal end of the flexible delivery system of the invention, illustrating how a state-of-the-art robotic positioning device may be used to insert and withdraw a probe rotatably supported by the system into and out of a selected heat exchanger tube in a nuclear steam generator.
Figure 1B:
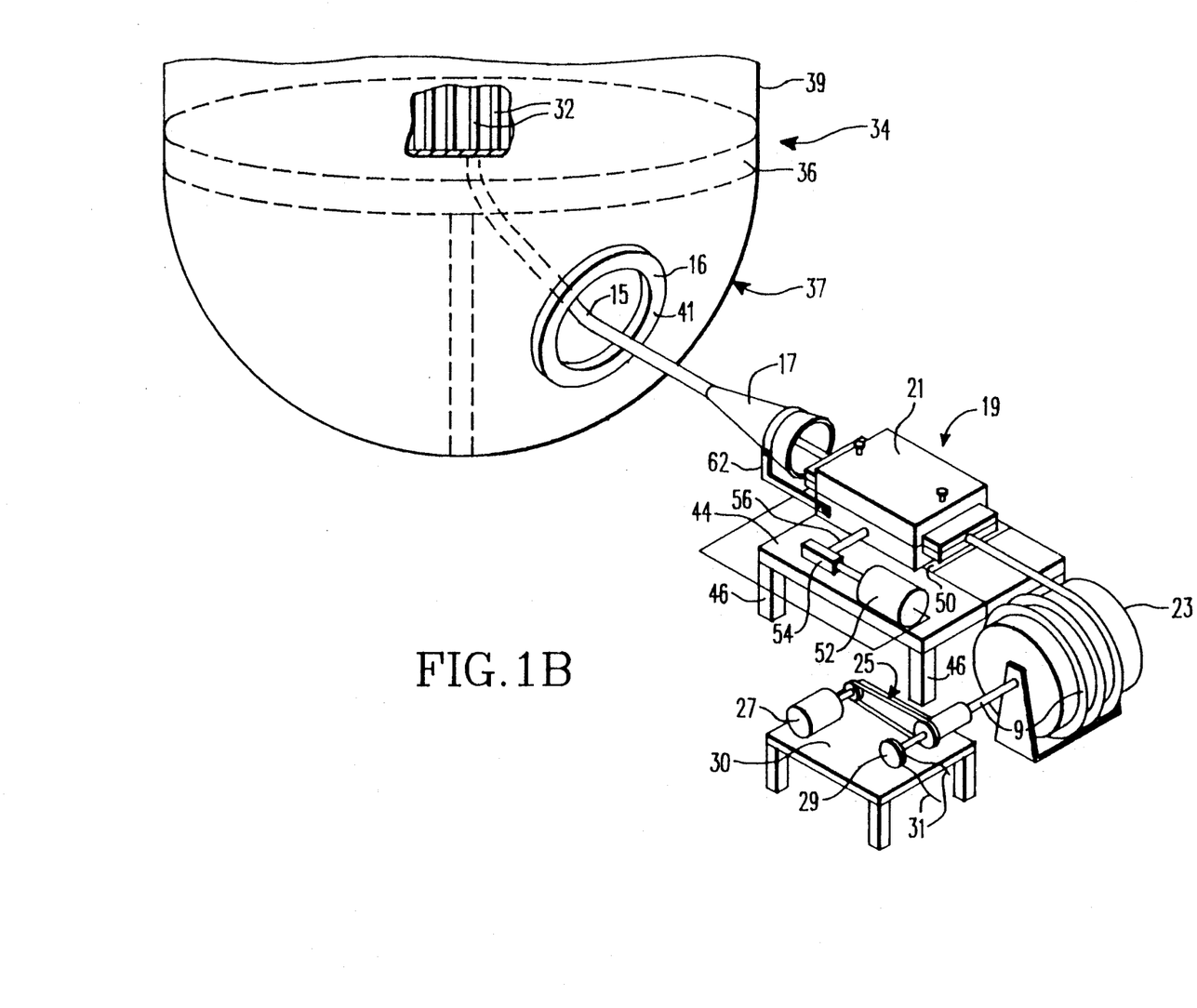
FIG. 1B is a perspective view of the proximal end of the system, illustrating how it may be moved into and out of a manway in the primary side of a nuclear steam generator by means of a known pusher-puller mechanism.

With reference now to FIGS. 1A and 1B, wherein like reference numerals designate like components throughout all the several figures, the purpose of the flexible delivery system 1 of the invention is to deliver and to rotatably support a probe 2 which may be a rotating, pancake-type eddy current probe within a small-diametered conduit, such as the heat exchanger tubes of a nuclear steam generator. The probe 2 includes an elongated, cylindrical housing 3 in which a pancake-type eddy current coil 4 is radially and resiliently mounted. The system further includes a flexible shaft segment 5 located just beneath the probe housing 3, and an encoder housing assembly 7 located just beneath the flexible shaft segment 5. Finally, the system includes a flexible cable 9 for transmitting both torque and electrical power to the probe 2. The flexible cable 9 is formed from a rotatable inner shaft assembly 11 that is contained within a non-rotatable, flexible outer housing 13 which, in the preferred embodiment, is formed from plastic tubing. A pair of coaxial cables 12a,b are disposed within the inner shaft assembly 11 for conducting alternating current to the coil 4 and to an encoder which will be described in more detail presently. A robotic positioner 14 (schematically illustrated in phantom) is used to insert and to withdraw the probe 2 and the flexible cable 9 into and out of a selected heat exchanger tube within a nuclear steam generator.

With reference now to FIGS. 1A and 1B, a guide tube 15 is used to guide the probe 2 and flexible cable 9 into and out of an open manway 16 located at the lower portion of the steam generator. The proximal end of the guide tube 15 terminates in a funnel 17 which helps to lead the probe 2 and flexible cable 9 initially into the guide tube 15 from a pusher-puller mechanism 19. In the preferred embodiment, the pusher-puller mechanism 19 may be a single or a multiple probe insertion device such as that disclosed and claimed in co-pending U.S. patent application Ser. No. 375,989, filed Jul. 6, 1989, and now U.S. Pat. No. 5,105,876 by Robert D. Burack et al. and assigned to the Westinghouse Electric Corporation. Such mechanisms 19 include a drive unit 21 which, as has been mentioned previously, contain opposing, resiliently mounted drive wheels which engage the flexible cable 9, and push it into or pull it out of the guide tube 15 disposed in the manway 16. Located directly behind the drive unit 21 is a reel 23 for storing and supporting the proximal portion of the flexible cable 9. The proximal end of the cable 9 extends out of the side of the reel 23 so that the proximal end of the inner shaft assembly 11 may be mechanically connected to a drive train 25 powered by an electric motor 27. Also connected to the proximal end of the inner shaft assembly is a slip ring 29 which is rotatably mounted upon a table-like platform 30. The purpose of the slip ring 29 is to conduct electrical current to the coaxial cables 12a,b disposed through the center of the inner shaft assembly 11 despite the rotational movement of these cables 12a,b by the drive train 25. To this end, the slip ring 29 includes a pair of leads 31 which may be connected, for example, to a MIZ-18 multiple frequency generator manufactured by Zetec located in Isaquah, Wash., and various encoder processing circuits (not shown).

As has been previously indicated, the primary purpose of the flexible delivery system 1 is to deliver and rotatably support a probe 2 within a heat exchanger tube 32 of a nuclear steam generator 34. The open ends of such heat exchanger tubes 32 are mounted in a tubesheet 36 which hydraulically isolates but thermally connects the primary side 37 of the generator 34 located beneath the tubesheet 36 to the secondary side 39 disposed over the tubesheet 36. If the delivery system 1 is to fulfill this purpose, its outer diameter can be no larger than between about 0.50 and 0.625 inches (1.27–1.59 cm); otherwise, it will not fit into the inner diameter of the heat exchanger tube 32.

Figure 2A:
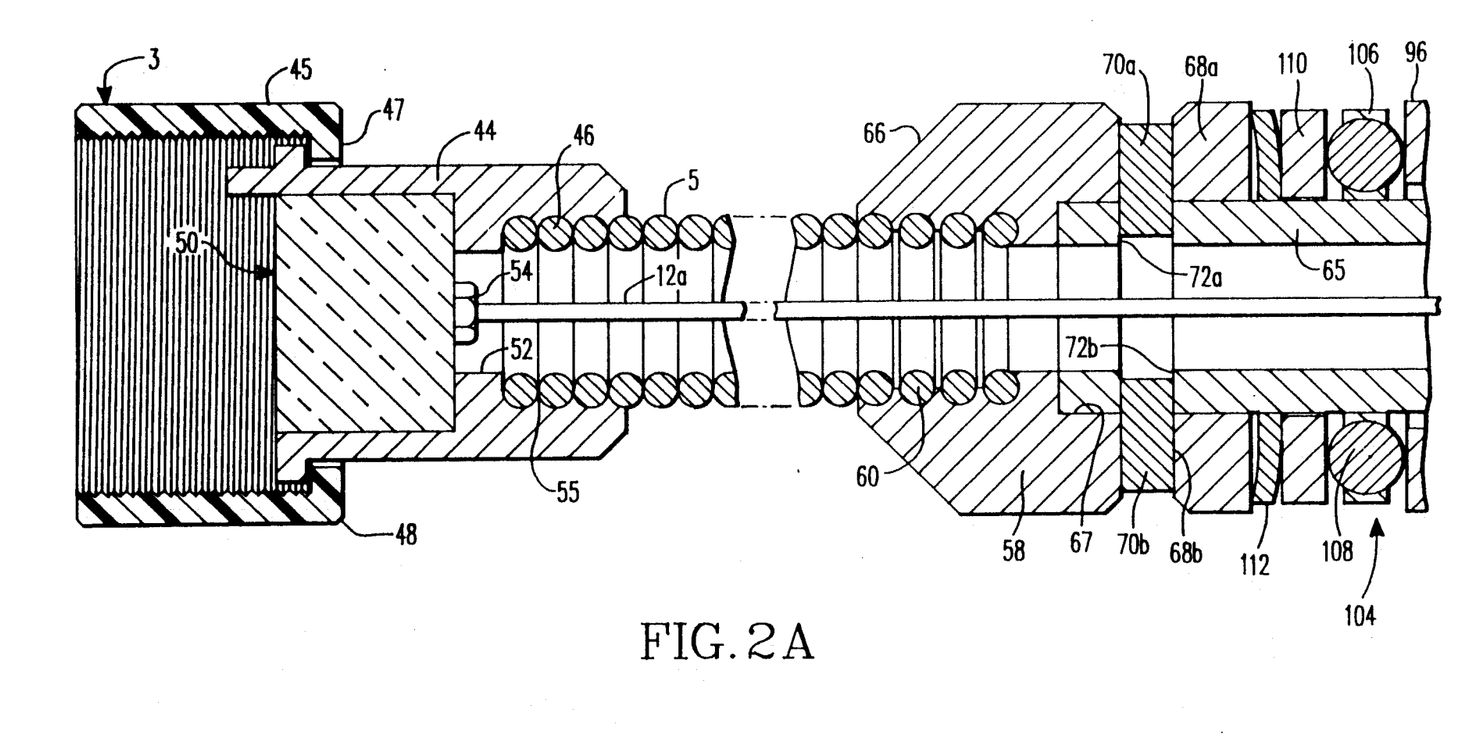
FIGS. 2A and 2B, hereinafter collectively referred to as FIG. 2, are a side, cross-sectional view of the delivery system of the invention, illustrating both the encoder housing assembly of the system, and how the system rotatably supports the housing of a probe.
Figure 2B:
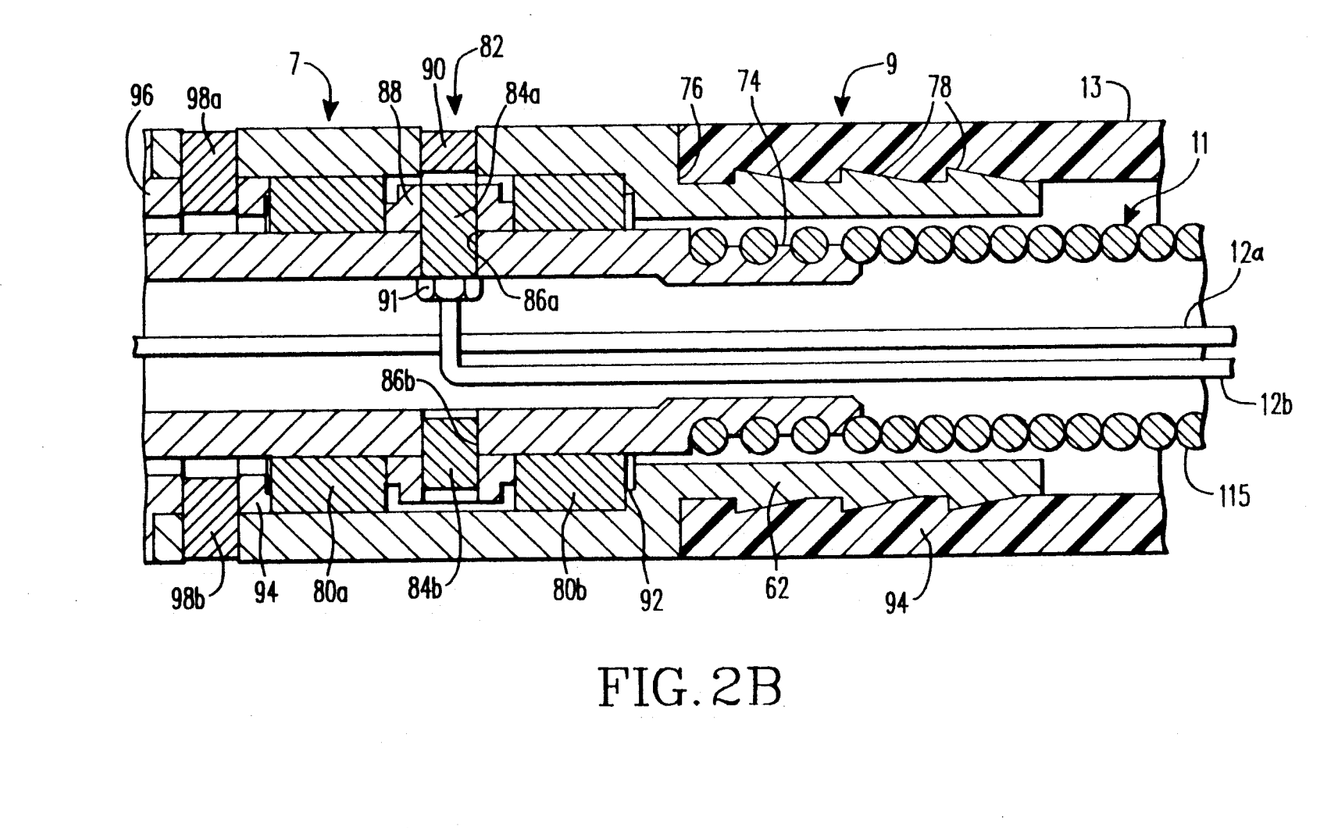

With reference now to FIG. 2, a coupling 44 is provided for connecting the proximal end 45 of the probe housing 3 to the distal end 46 of the shaft segment 5. The coupling includes an annular shoulder 47 that circumscribes its distal end which is captured by a flange 48 located at the proximal end 45 of the probe body 3. Disposed within the coupling 44 at its distal end is an electrical connector assembly 50 which is supported by an internal annular shoulder 52. The electrical connector assembly 50 includes sockets for receiving pins (not shown) which are in turn connected to the leads of the pancake-type eddy current coil 4 disposed within the probe 2. These sockets are in turn connected to the coaxial cable 12, which is secured to the proximal end of the electrical connector assembly 50 by means of a nut 54. The proximal end of the coupling 44 includes a threaded recess 55 into which the distal end 46 of the shaft segment 5 is screwed. While the flexible shaft segment 5 may be formed from any one of several different types of commercially-available flexible shaft material, Bowden shafting is preferred due to its high strength and low weight. Such shafting material generally resembles a tight coil spring formed from spring steel in which adjacent coils come into contact with one another. The pitch of the spring steel coils which forms such shaft material forms a natural screw thread which can be engaged directly within the threaded recess 55 of the coupling 44.

A distal shaft coupling 58 connects the proximal end 60 of the flexible shaft segment 5 to the encoder housing assembly 7. Similarly, a proximal cable coupling 62 connects the distal end 64 of the flexible cable 9 to the proximal end of the encoder housing assembly 7. A support sleeve 65 connects the distal shaft coupling 58 with the proximal coupling 62. The relationship between these three components will now be described in greater detail.

The distal end of the shaft coupling 58 includes a conical leading edge 66, while its proximal end includes a cylindrical recess 67 for receiving the end of the support sleeve 65. The coupling 58 further includes a pair of radially disposed bores 68a,b for receiving a pair of securing pins 70a,b. These same securing pins 70a,b are receivable within opposing bores 72a,b present in the support sleeve 65. The proximal end of the support sleeve 65 includes threads 74 which are engageable with the distal end of one of the segments of Bowden shafting forming the inner shaft assembly 11. Hence, torque conducted through the inner shaft assembly 11 is conducted through the support sleeve 65 and from thence to the distal shaft coupling 58 and onward to the probe housing 3 through the flexible segment 5. The proximal cable coupling 62 concentrically overlies the proximal end of the support sleeve 65. The proximal end of the cable coupling 62 includes an annular recess 76 which is circumscribed by a plurality of barbed flanges 78 for receiving and securing the distal end of the flexible outer housing 13 to the cable coupling 62. A pair of bearings 80a,b are disposed between the outer diameter of the support sleeve 65 and the inner diameter of the proximal cable coupling 62 to minimize friction therebetween when the sleeve 65 rotates relative to the coupling 62.

An encoder assembly 82 is disposed between the bearings 80a,b which includes a pair of tick coils 84a,b. Each of these coils is mounted within a bore 86a,b provided in the central portion of the support sleeve 65. The outer ends of each of the tick coils 84a,b are encased in a plastic housing 88. A ferrite target 90 is secured within a bore present in the proximal cable coupling 62 in the same plane of rotation as the tick coils 84a,b. A securing nut 91 connects these tick coils 84a,b to one of the coaxial cables 12b that is disposed throughout the center of the inner shaft assembly 11. Coaxial cable 12b is, in turn, connected to a commercially-available encoder circuit (not shown). In operation, an alternating current is conducted through the tick coils 84a,b through the coaxial cable 12b. Whenever one of the coils 84a,b comes into alignment with the ferrite target 90, the electro-magnetic coupling between the field emanated by the coil 84a,b and the material forming the target 90 creates a change in impedance in the coils which in turn is detected by the encoder circuit (not shown). By measuring the periodicity of these impedance changes, the system operation can determine the rotational speed of the support sleeve 65, which in turn indicates the rotational speed of the probe housing 3.

The bearings 80a and 80b reduce the friction between the encoder housing assembly 7 and support sleeve 65. Bearing 80b is captured between an internal annular shoulder 92 and one side of the housings 88 surrounding the tick coils 84a,b, while bearing 80a is captured between these same housings and the proximal end 94 of a bearing cap connector 96. The bearing cap connector 96 is in turn secured onto the distal end of the cable coupling 62 by means of securing pins 98a,b which are insertable within mutually registrable bores present in the coupling 62 and the bearing cap connector 96. A thrust bearing 104 is provided between the non-rotating cable coupling 62, and the rotating shaft coupling 58 to reduce friction at this interface. The thrust bearing 104 is formed from a bearing retainer 106 into which a plurality of ball bearings 108 are slidably captured. A washer 110 in combination with a Bellville spring 112 biases the ball bearings 108 within the bearing retainer 106 against the previously mentioned bearing cap connector 96 to eliminate slack.

Figures 3A, 3B:
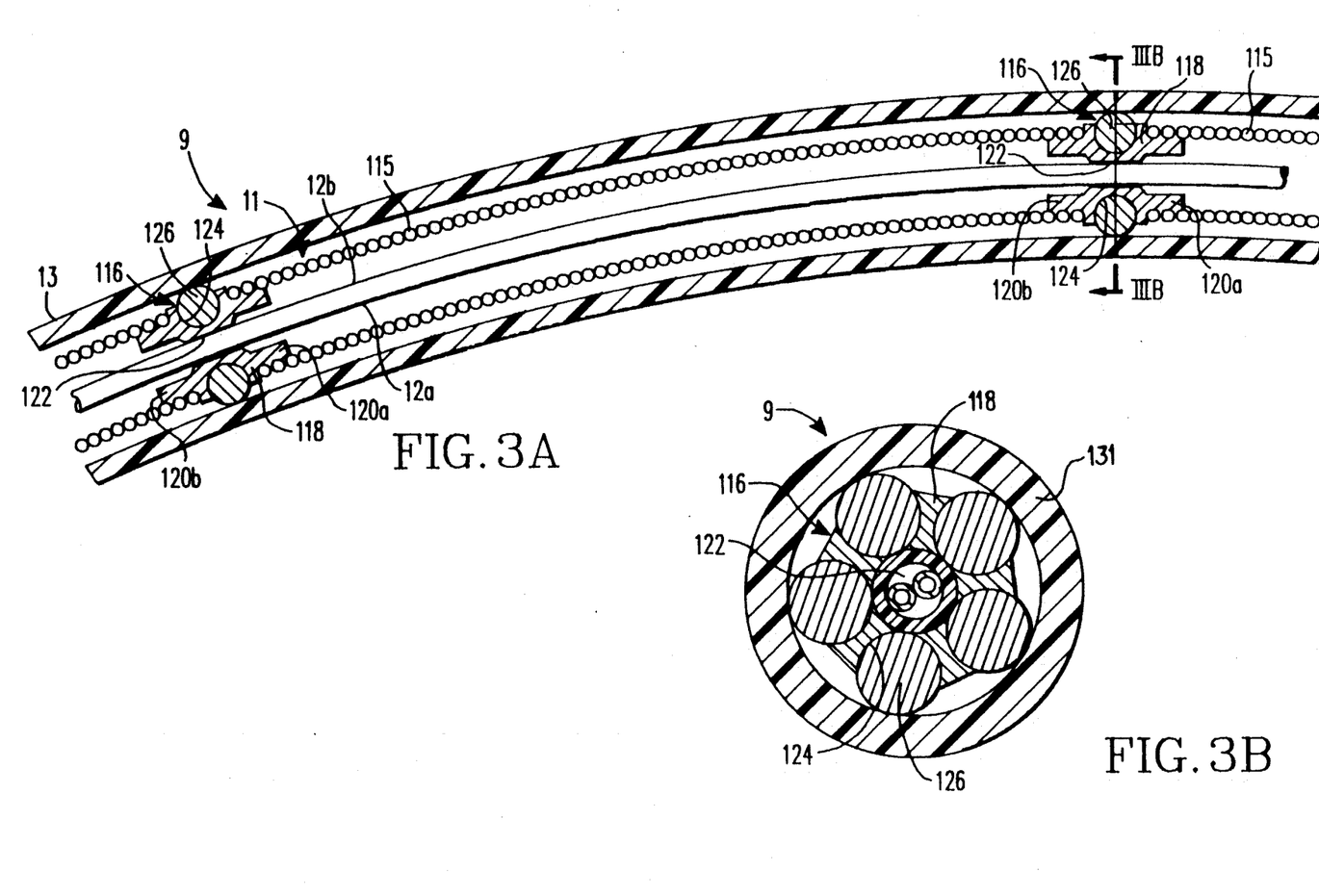
FIG. 3A is a side, cross-sectional view of the flexible cable used to remotely transmit torque from a drive train located out of the primary side of a nuclear steam generator to the probe.
FIG. 3B is a cross-sectional view of the flexible cable illustrated in FIG. 3A along the lines 3B—3B, showing details of the structure of the bearing assemblies used to minimize friction between the inner shaft assembly, and the flexible outer housing of the flexible cable.

With reference now to FIGS. 3A and 3B, the flexible cable 9 includes an inner shaft assembly 11 disposed within a hose-like flexible outer housing 13. The inner shaft assembly 11 is formed from a plurality of relatively short shaft segments 115 made from the same Bowden shaft material at the previously discussed shaft segment 5. A plurality of shaft bearing assemblies 116 serve the dual function of interconnecting the shaft segments 115, and minimizing friction between the inner shaft assembly 11 and the inner wall of the flexible outer housing 13. Each of the shaft bearing assemblies includes a housing sleeve 118 having opposing, threaded ends 120a,b onto which the ends of adjacent shaft segments 115 may be screwed. A cable passageway 122 is disposed throughout the center of each of the housing sleeves 118 for conducting the previously mentioned pair of coaxial cables 12a,b. Disposed around the outer periphery of each of the housing sleeves 118 is a plurality of semi-spherical bearing recesses 124. In the preferred embodiment, five such recesses are provided, although as few as three may be used. Each of the bearing recesses 124 rollingly receives a ball bearing 126. In the preferred embodiment, each of the shaft segments 115 is of equal length, and the segments 115 are sufficiently short so that no segment 115 comes into direct contact with the inner wall of the surrounding flexible outer housing 13 when the flexible cable 9 is coiled around the reel 23 that feeds the cable 9 into the pusher-puller mechanism 19.

Figure 4:
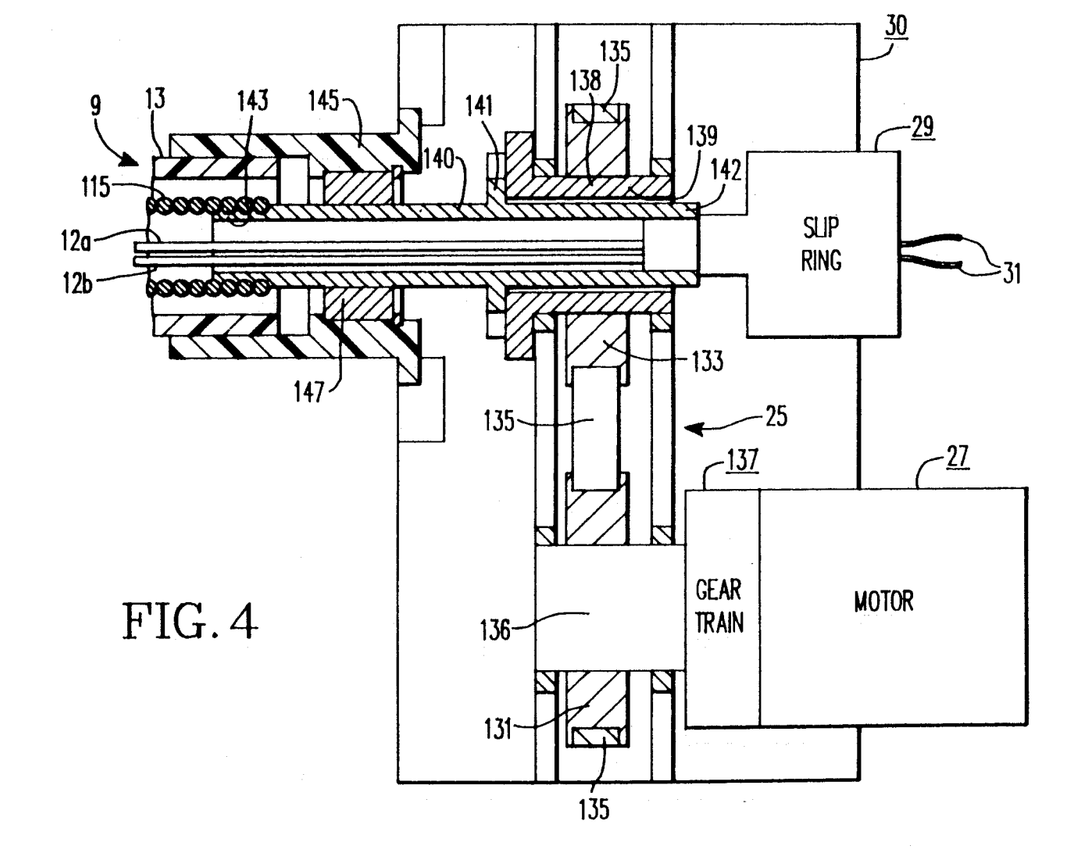
FIG. 4 is a cross-sectional view of the drive train, motor and slip ring of the system used to drive the rotatable inner shaft assembly of the system and to conduct electricity through the inner shaft to the coil of the probe mounted at the distal end of the flexible cable.

With reference now to FIG. 4, the drive train 25 that is connected to the proximal end of the flexible shaft segment 5 is provided with a drive pulley 131 that in turns rotates a driven pulley 133 by way of a belt 135. The drive pulley 131 is connected to the output shaft 136 of a gear train 137 which is turn is coupled to the output shaft (not shown) of the previously mentioned electric motor 127. The driven pulley 123 is in turn connected to a shaft 138 rotatably mounted onto the table-like platform 30 that has a centrally disposed bore 139. A coupler sleeve 140 is received within the bore 139 of the shaft 138. This sleeve includes a connecting flange 141 which is bolted or otherwise secured onto the front edge of the shaft 138. The proximal end of the coupler sleeve 140 is connected to the output of the previously mentioned slip ring 29, which in turn is secured and electrically connected to the proximal ends of each of the coaxial cables 12a,b. The distal end 143 of the coupler sleeve 140 is screwed into the coils of the most proximal of the shaft segments 115 forming the inner shaft assembly 11. A cable coupler 145 connects the proximal end of the flexible outer housing 13 of the cable 9 to the table-like platform 30. To minimize friction between the coupler 145 and the sleeve 140, a bearing 147 is provided in the position shown.

The operation of the system 1 of the invention may best be understood with reference to FIGS. 1A and 1B. First, the probe housing 3 and flexible cable 9 are unwound from the reel 9 and fed through the drive unit 21 of the pusher-puller mechanism 19 and from thence to the funnel 17 of the guide conduit 15. The robotic positioner 14 grasps the probe housing 3 of the system 1 as it exits the guide conduit 15. The robotic positioner 14 then proceeds to insert the probe housing 3 of the system 1 into the open end of a selected heat exchanger tube 32 until the coil 4 mounted within the probe housing 3 is directly adjacent a particular area of interest within the heat exchanger tube 32. At this juncture, the motor 27 of the drive train 25 is actuated while, at the same time, electrical currents are conducted through the coaxial cables 12a,b from the aforementioned variable frequency generator of the eddy current controller, and the encoder circuitry. In the preferred method of operation, the gear train 137 of the drive assembly 25 will be chosen so that the inner shaft assembly 11 is rotated at a rate of approximately 300 rpms. The rotational rate is constantly monitored by the system operator from the signals received from the previously described encoder assembly 82. A screw thread (not shown) mounted within the probe housing 3 converts the rotational movement of the housing 3 into a helical movement wherein the pancake coil 4 wipingly engages and helically scans the internal surface of the heat exchanger tube 32. After the coil 4 and traveled the maximum linear distance allowed by the aforementioned screw thread, the eddy current controller is shut down, and the direction of the motor 27 is reversed to re-position the pancake-type coil 4 into its proximal-most position within the probe housing 3. The process is then repeated after the robotic positioner 14 places the coil 4 adjacent to another area of interest within the same or a different heat exchanger tube 32.

I claim:

1. A flexible delivery system for positioning and rotatably supporting a probe at a desired position within a conduit along a central longitudinal axis of said conduit, comprising:

a flexible inner shaft having a distal end connected to said probe and a proximal end connected to a shaft rotating means;

a flexible outer housing concentrically disposed around said inner shaft, a plurality of bearing assemblies disposed between said inner shaft and said outer housing for reducing friction between said shaft and housing when said inner shaft rotates with respect to said outer housing, and a thrust bearing at an interface between said probe and said flexible outer housing for minimizing friction at said interface.

2. A flexible delivery system as defined in claim 1, wherein said flexible inner shaft is comprised of a plurality of shaft segments, and wherein said bearing assemblies include coupling means for coupling together said shaft segments.

3. A flexible delivery system as defined in claim 2, wherein said shaft segments are each formed from Bowden shafting material.

4. A flexible delivery system as defined in claim 2, wherein said bearing assemblies each include at least three ball bearings.

5. A flexible delivery system as defined in claim 1, wherein said bearing assemblies are uniformly spaced along a central longitudinal axis of the inner shaft.

6. A flexible delivery system as defined in claim 1, further comprising an electrical conductor assembly including a cable disposed within said flexible inner shaft for providing electrical current to said probe, wherein said cable rotates along with said inner shaft.

7. A flexible delivery system as defined in claim 6, wherein said electrical cable has a distal end connected to said probe, and a proximal end connected to a source of electricity and said conductor assembly includes a slip ring conductor for connecting said cable proximal end to said source of electricity.

8. A flexible delivery system as defined in claim 1, further comprising an encoder means located near the distal end of said inner shaft for monitoring rotational movement of said shaft relative to said housing.

9. A flexible delivery system as defined in claim 1, wherein said probe includes biasing means for biasing said probe against said thrust bearing.

10. A flexible delivery system for positioning and rotatably supporting a probe at a desired position within a tube along a central longitudinal axis of the tube, comprising:

a flexible inner shaft formed from a plurality of shaft segments arranged in tandem, said shaft having a distal end connected to said probe and a proximal end connected to a shaft rotating means;

a flexible outer housing concentrically disposed around said inner shaft and terminating at the connection between said flexible inner shaft and said probe, and a plurality of bearing assemblies, each of which includes a coupling means for connecting together two in-tandem shaft segments of said inner shaft, each bearing assembly further including a bearing means disposed between said inner shaft and said outer housing for reducing friction between said shaft and housing.

11. A flexible delivery system as defined in claim 10, wherein each of said shaft segments is formed from a flexible material.

12. A flexible delivery system as defined in claim 11, wherein each of said shaft segments is formed from Bowden shafting.

13. A flexible delivery system as defined in claim 10, wherein said bearing means includes at least three ball bearings uniformly spaced around a circumference of its respective bearing assembly.

14. A flexible delivery system as defined in claim 10, wherein each of said shaft segments is of substantially the same length.

15. A flexible delivery system as defined in claim 10, further comprising an electrical conductor assembly including a cable disposed within said flexible inner shaft for providing electrical current to said probe, wherein said cable rotates along with said inner shaft.

16. A flexible delivery system as defined in claim 15, wherein said electrical cable has a distal end connected to said probe, and a proximal end connected to a source of electricity and said conductor assembly includes a slip ring conductor for connecting said cable proximal end to said source of electricity.

17. A flexible delivery system as defined in claim 10, further comprising an encoder means located near the distal end of said inner shaft for monitoring rotational movement of said shaft relative to said housing.

18. A flexible delivery system as defined in claim 17, wherein said encoder means includes a tick coil mounted in said flexible outer housing and a ferrite target pin mounted on the inner shaft.

19. A flexible delivery system as defined in claim 18, wherein said flexible outer housing includes a tube of flexible plastic material.

20. A flexible delivery system for positioning and rotatably supporting a probe at a desired position within a tube along a central longitudinal axis of the tube, comprising:

a flexible inner shaft formed from a plurality of flexible, tubular shaft segments arranged in tandem, said shaft having a distal end connected to said probe and a proximal end connected to a shaft rotating means;

a flexible, tubular outer housing concentrically disposed around said inner shaft and terminating at the connection between said flexible inner shaft and said probe, and a plurality of bearing assemblies, each of which includes a coupling means for connecting together two, in-tandem shaft segments of said inner shaft, each bearing assembly further including at least three uniformly spaced ball bearings disposed between said inner shaft and said outer housing for reducing friction between said shaft and housing.

21. A flexible delivery system as defined in claim 20, wherein each of said bearing assemblies includes a bore in alignment with the hollow interiors of the two in-tandem shaft segments, the delivery system further comprising a conductor assembly including an electrical cable disposed within said flexible inner shaft for providing electrical current to said probe, wherein said cable rotates along with said inner shaft.

22. A flexible delivery system as defined in claim 21, wherein said electrical cable has a distal end connected to said probe, and a proximal end connected to a source of electricity and said conductor assembly includes a slip ring conductor for connecting said cable proximal end to said source of electricity.

23. A flexible delivery system as defined in claim 20, wherein each of said shaft segments is formed from Bowden shafting.

24. A flexible delivery system as defined in claim 20, wherein said shaft rotating means is the output shaft of a gear train connected to a motor means.

25. A flexible delivery system for positioning and rotatably supporting a probe at a desired position within a conduit along a central longitudinal axis of said conduit, comprising:
- a flexible inner shaft having a distal end connected to said probe and a proximal end connected to a shaft rotating means;
- a flexible outer housing concentrically disposed around said inner shaft, and
- a plurality of bearing assemblies disposed between said inner shaft and said outer housing for reducing friction between said shaft and housing when said inner shaft rotates with respect to said outer housing, wherein each of said bearing assemblies is connected to said flexible inner shaft and includes a plurality of ball bearings rotatably mounted in said assembly capable of rollingly traversing the interior of the outer housing in both the circumferential and longitudinal directions.

* * * * *